United States Patent [19]
Slater et al.

[11] Patent Number: 5,347,995
[45] Date of Patent: Sep. 20, 1994

[54] LARYNGOSCOPE BLADE COVER

[76] Inventors: William M. Slater, 3221 Fairway Dr., Las Cruces, N. Mex. 88001; Anthony M. Chiasson, 4056 Knob Hill Dr., Muskegon, Mich. 49441-4187; Thomas A. Denny, 3609 Crescent Ave., Farmington, N. Mex. 87401

[21] Appl. No.: 37,615

[22] Filed: Mar. 25, 1993

[51] Int. Cl.⁵ ............................................ A61B 1/26
[52] U.S. Cl. ............................................ 128/10; 128/4; 128/17; 206/363; 206/805; 604/163; 359/511
[58] Field of Search ............. 128/10, 11, 17, 18, 128/4; 206/805, 363, 438, 306; 150/154, 161; 604/163, 171, 263; 359/507, 510, 511, 512

[56] References Cited

U.S. PATENT DOCUMENTS

| | | | |
|---|---|---|---|
| 1,929,338 | 10/1933 | Tichenor | 206/306 |
| 2,070,820 | 2/1937 | Allyn | 128/11 |
| 2,289,226 | 7/1942 | Foregger | 128/16 |
| 2,648,329 | 8/1953 | Morch | 128/11 |
| 3,426,433 | 2/1969 | Anderson | 359/511 X |
| 3,426,749 | 2/1969 | Jephcott | 128/11 |
| 3,752,309 | 8/1973 | Hopkins et al. | 206/363 X |
| 3,794,091 | 2/1974 | Ersek et al. | 128/23 X |
| 3,851,642 | 12/1974 | McDonald | 128/18 |
| 3,856,001 | 12/1974 | Phillips | 128/11 |
| 4,344,419 | 8/1982 | Burgin | 128/18 |
| 4,425,909 | 1/1984 | Rieser | 128/16 |
| 4,522,196 | 6/1985 | Cunningham et al. | 128/4 |
| 4,579,108 | 4/1986 | Bauman | 128/10 |
| 4,583,527 | 4/1986 | Musicant et al. | 128/11 |
| 4,741,326 | 5/1988 | Sidall et al. | 128/4 |
| 4,834,077 | 5/1989 | Sun | 128/11 |
| 4,878,486 | 11/1989 | Slater | 128/11 |
| 4,884,558 | 12/1989 | Gorski et al. | 128/11 |
| 4,972,825 | 11/1990 | Vescovo, Jr. | 128/10 |
| 4,979,499 | 12/1990 | Sun | 128/11 |
| 5,030,210 | 7/1991 | Alchas | 604/247 |
| 5,063,907 | 11/1991 | Musicant et al. | 128/10 |
| 5,065,738 | 11/1991 | Van Dam | 128/11 |
| 5,150,528 | 9/1992 | Shire | 359/511 X |

FOREIGN PATENT DOCUMENTS

| | | | |
|---|---|---|---|
| 2737710 | 3/1979 | Fed. Rep. of Germany | 206/438 |
| 1079345 | 8/1967 | United Kingdom | 206/306 |

*Primary Examiner*—Richard J. Apley
*Assistant Examiner*—Donna L. Maraglio
*Attorney, Agent, or Firm*—Emch, Schaffer, Schaub & Porcello Co.

[57] ABSTRACT

A disposable laryngoscope blade cover that includes a flexible sleeve and a resilient slide band for use in conjunction with a laryngoscope having a blade and a handle. The sleeve has an open end and a closed end. The open end is received by the blade and the handle. The sleeve covers the blade and at least a portion of the handle. The resilient slide band is fixedly attached to the sleeve. The band engages the handle to maintain the sleeve on the laryngoscope. After the cover has been used, the band can be disengaged from the handle for removal of the sleeve from the laryngoscope. The invention is also directed to a method for maintaining the sterility of the cover. The steps include the following: (a) providing a sterile cover consisting of a flexible sleeve having an open end and a closed end and a resilient slide band contained within a flexible protective package; (b) opening the package thereby exposing the open end of the cover; (c) inserting the blade into the open end of the sleeve; (d) pulling the slide band to cause the sleeve to completely cover the blade and at least a portion of the handle; and (e) engaging the slide band to the handle to maintain the sleeve on the laryngoscope.

8 Claims, 2 Drawing Sheets

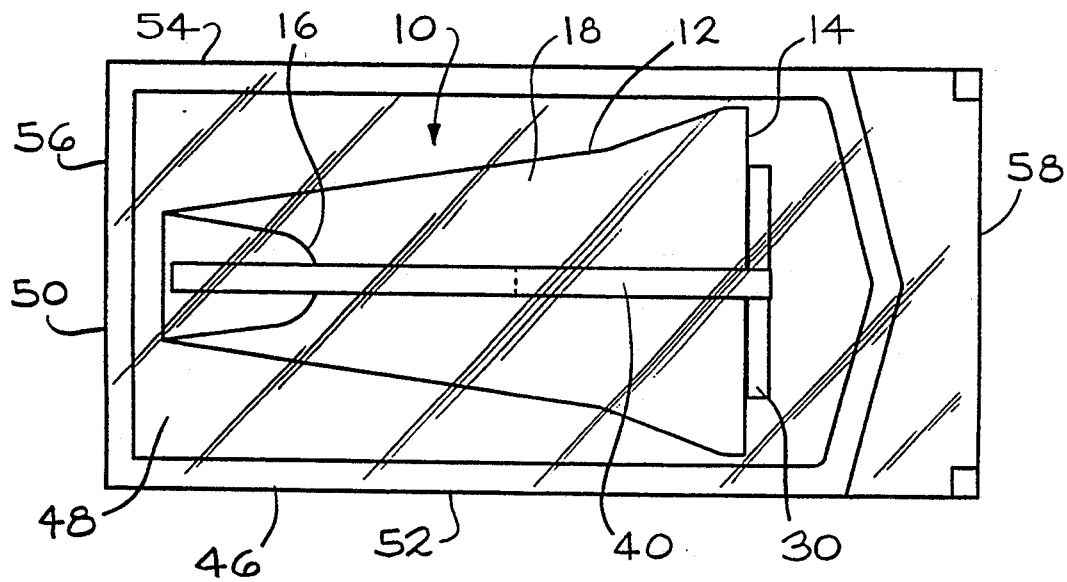
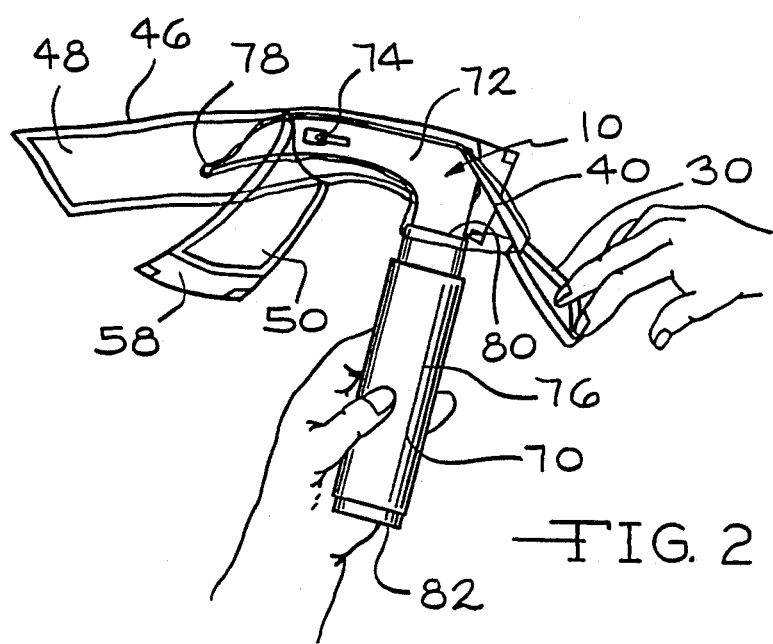

LARYNGOSCOPE BLADE COVER

DESCRIPTION

Background Art

The present invention is directed to a laryngoscope blade cover. More specifically, the invention is directed to a disposable laryngoscope blade cover having a flexible sleeve and a resilient slide band to attach the sleeve to a laryngoscope.

A laryngoscope is a device that is used by a physician to examine a patient's throat. The device consists generally of a blade movably attached to a cylindrically shaped handle. The blade can have a variety of shapes, but usually it has a curved, elongated shape that conforms to the shape of a patient's throat. The blade has an internal channel with a light source so that a physician can look through the blade and into a throat. The handle is used to manipulate the blade and also to contain a power source for the light.

In recent years it has become important that a laryngoscope blade remain sterile in order to prevent the transmission of serious diseases. It has been found that it is difficult and expensive to sterilize permanent blades. This fact led to the development of disposable laryngoscope blade covers. Examples of prior art disposable covers are shown in U.S. Pat. Nos. 3,426,749; 4,579,108; 4,583,527; 4,834,077; 4,878,486; 4,972,825; 4,979,499; 5,063,907; and 5,065,738. It has been found that these prior art covers are too expensive, too difficult to use and too opaque.

The present invention provides a disposable cover that is relatively inexpensive, easy to use and translucent as compared to prior art covers.

Disclosure of Invention

The present invention is a disposable laryngoscope blade cover that includes a flexible sleeve and a resilient slide band for use in conjunction with a laryngoscope having a blade and a handle. The sleeve has an open end and a closed end. The open end is received by the blade and the handle. The sleeve covers the blade and at least a portion of the handle.

The resilient slide band is fixedly attached to the sleeve. The band engages the handle to maintain the sleeve on the laryngoscope. After the cover has been used, the band can be disengaged from the handle for removal of the sleeve from the laryngoscope.

The invention is also directed to a method for maintaining the sterility of the cover. The steps include the following: (a) providing a sterile cover consisting of a flexible sleeve having an open end and a closed end and a resilient slide band contained within a flexible protective package; (b) opening the package thereby exposing the open end of the cover; (c) inserting the blade into the open end of the sleeve; (d) pulling the slide band to cause the sleeve to completely cover the blade and at least a portion of the handle; and (e) engaging the slide band to the handle to maintain the sleeve on the laryngoscope.

It is the primary object of the present invention to provide an inexpensive disposable laryngoscope cover.

It is an important object of the present invention to provide a laryngoscope cover that is easy to use.

It is an important object of the present invention to provide a translucent laryngoscope cover.

Other objects and advantages of the invention will become apparent as the invention is described hereinafter in detail with reference to the accompanying drawings.

BRIEF DESCRIPTION OF THE DRAWINGS

FIG. 1 is a plan view of the laryngoscope blade cover according to the present invention contained within a protective package;

FIG. 2 is a perspective view of the laryngoscope blade cover according to the present invention being positioned on the blade of a laryngoscope;

BEST MODE FOR CARRYING OUT INVENTION

Figure 5:
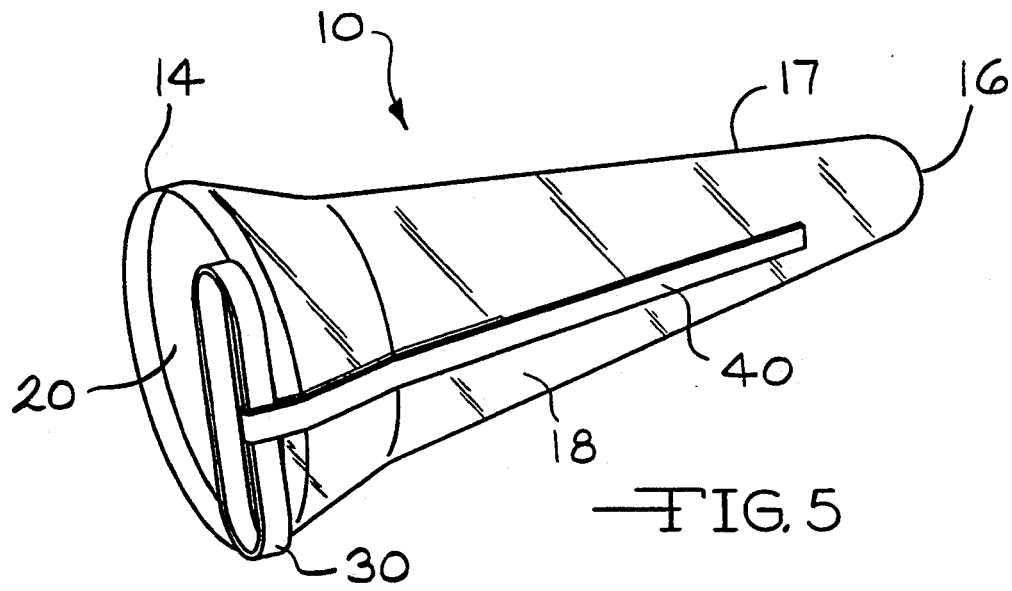
FIG. 5 is a perspective view of the laryngoscope blade cover according to the present invention.

Referring now to the drawings, the laryngoscope blade cover of the present invention is designated by the reference number 10. Referring to FIGS. 1 and 5, the cover 10 includes a flexible sleeve 12. The sleeve 12 has an elongate shape that conforms to the shape of a laryngoscope blade. The sleeve can be made of a variety of translucent materials. It has been found that polymeric materials are especially suitable, with polyurethane being preferred because of its physical properties. The polymeric material should have a thickness of between 0.05 mil and 3 mils, with a 1.5 mil thickness being preferred. This thickness range allows the material to be flexible enough so that it may tightly envelope the blade while allowing for translucence. The sleeve 12 includes an open end 14 and a closed end 16. The sleeve 12 further includes an exterior surface 18 and an interior surface 20.

Still referring to FIGS. 1 and 5, the cover 10 includes a resilient circular slide band 30. The band can consist of a variety of elastomeric materials, with latex being preferred. It has also been found that flexible polymeric materials, such as plastic, can be used to make the band 30. The band 30 is fixedly attached to the sleeve 12. As shown in FIG. 5, the band 30 is attached to the sleeve by tape 40 that has been looped through the band 30 and attached by adhesive to the exterior and interior surfaces 18 and 20 of the sleeve 12. The tape 40 used in the present embodiment is an adhesive paper tape. However, it will be recognized by those skilled in the art that a variety of tapes can be used. It will also be recognized that the band 30 can be directly attached to the sleeve with or without tape.

Referring to FIG. 1, the cover 10 is shipped to users in a protective flexible package 46. The package 46 can be a variety of shapes but is usually a rectangular shape as shown in FIG. 1. The package 46 is usually made of a clear polymeric material that is flexible enough for manipulation and sufficiently rigid so that it does not break during shipping thereby exposing the cover to contaminants. The package 46 includes a two protective sheets 48 and 50 that sandwich the cover 10. Each sheet includes a first side 52, a second side 54, a first end 56 and a second end 58. The respective sides and ends are releasably sealed together.

Figure 3:
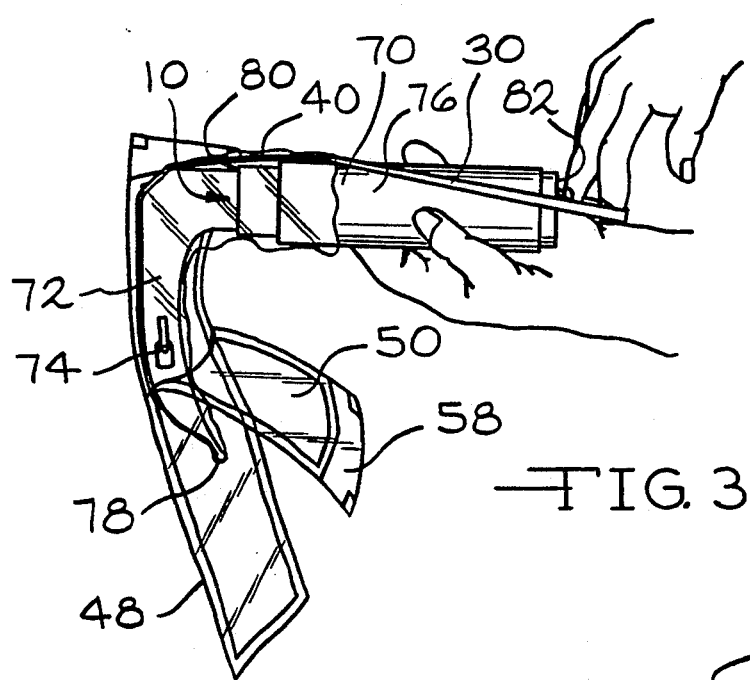
FIG. 3 is a perspective view of the laryngoscope blade cover according to the present invention being positioned on the handle of a laryngoscope.
Figure 4:
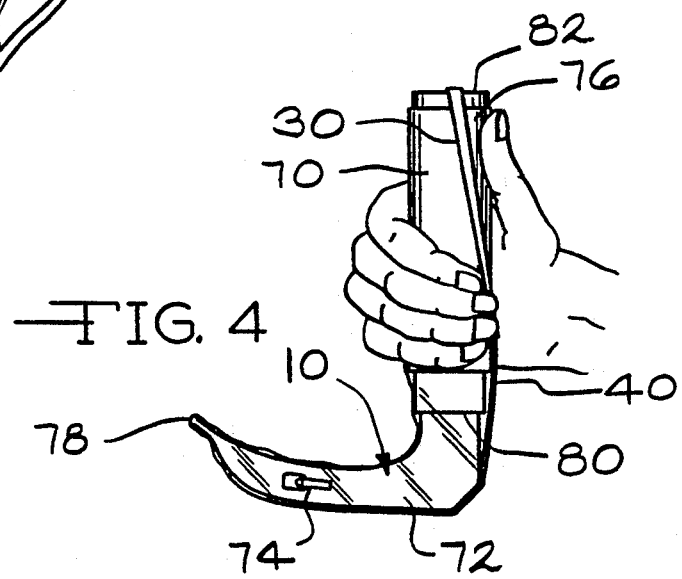
FIG. 4 is a perspective view of the laryngoscope blade cover according to the present invention in position on a laryngoscope ready for use.

Referring now to FIGS. 2–4, the method attaching the cover 10 to a laryngoscope is shown. The method provides for the maintenance of the sterility of the cover 10 while it is being attached to the laryngoscope. Referring first to FIG. 2, the laryngoscope 70 includes a blade 72 having a light 74 and a handle 76. The blade can have a variety of shapes with C-shaped and L-shaped lateral cross-sectional shapes being common. The blade usually has a rounded tip 78 to help the physician guide the blade 72 into a patient's throat. The opposite end of the blade 72 is pivotally attached to a handle having a blade attachment end 80 and a base end 82.

Still referring to FIG. 2, at the time that the laryngoscope is to be used, the protective package 46 is opened at the second end 58 and the sheets 48 and 50 are separated thereby providing access to the sterile cover 10. The opening of the package 46 exposes the open end 14 of the sleeve 12. The blade 72 of the laryngoscope 70 is inserted in the open end 14. The slide band 30 is then pulled to cause the sleeve 12 to completely cover the blade 72. As shown in FIG. 3, the slide band 30 continues to guide the sleeve 12 down the handle 76 thereby covering at least a portion of the handle. When the sleeve 12 is in its final position, the slide band 30 engages the base end 82 of the handle 76. The protective package 46 is then removed from the exterior surface 18 of the sleeve 12. The laryngoscope is then free to be used on a patient as shown in FIG. 4. The present invention allows the laryngoscope to be used without interference because the sleeve closely conforms to the shape of the blade and is highly translucent. After the cover 10 has been used, it can be removed by disengaging the slide band 30 from the base end 82 and removing the sleeve 12 from the blade. The cover 10 can be disposed.

The above detailed description of the present invention is given for explanatory purposes. Numerous changes and modifications can be made to the invention without departing from the scope of the appended claims.

We claim:

1. A laryngoscope blade cover comprising, in combination:
   a tapered, elongated, flexible sleeve having an open end and a closed end, wherein said open end is larger than said closed end, and an exterior surface and an interior surface, said open end adapted to be received by the blade of a laryngoscope and the handle of a laryngoscope, said sleeve adapted for covering completely said bland and at least a portion of said handle, and
   a resilient circular slide band fixedly attached to said sleeve adjacent said open end, by adhesive tape looped through said band and adhered to said exterior and interior surfaces of said sleeve, said band adatped to guide said sleeve over said blade and engage said handle to maintain said sleeve on said laryngoscope, said band allowing for disengagement from said handle for removal of said sleeve from said laryngoscope.

2. The laryngoscope blade cover of claim 1, wherein said flexible sleeve consists of a polymeric material.

3. The laryngoscope blade cover of claim 2, wherein said polymeric material is polyurethane.

4. The laryngoscope blade cover of claim 2, wherein said polymeric material has a thickness of from 0.05 mil to about 3 mils.

5. The laryngoscope blade cover of claim 1, wherein the shape of said sleeve conforms to the shape of said laryngoscope blade, 6. The laryngoscope blade cover of claim 1, wherein said slide band consists of an elastomeric material.

7. The laryngoscope blade cover of claim 6, wherein said elastomeric material is latex.

8. A method for maintaining the sterility of a laryngoscope blade cover while attaching such cover to a laryngoscope including the steps of:
   (a) providing a sterile cover consisting of a tapered, elongated, flexible sleeve having an open end and a closed end wherein said open end is larger than said closed end, an exterior surface and an interior surface, and a resilient slide band fixedly attached to said sleeve adjacent said open end, by adhesive tape looped through said band and adhered to said exterior and interior surfaces of said sleeve, all of which are contained within a flexible protective package consisting of two protective sheets that envelope said cover, each of said sheets including a first side, a second side, a first end and a second end, said respective sides and ends being releasably sealed together;
   (b) separating said sheets at said second end of said flexible package thereby exposing said open end of said cover;
   (c) inserting the blade and the handle of a laryngoscope into said open end of said sleeve;
   (e) pulling said slide band to guide said sleeve over said blade and to cause said sleeve over said blade and to cause said sleeve to completely cover said blade and at least a portion of said handle; and
   (e) engaging said slide band to said handle to maintain said sleeve on said laryngoscope.

* * * * *